(12) United States Patent
Orvar (10) Patent No.: US 7,428,875 B2
(45) Date of Patent: Sep. 30, 2008

(54) TRACEABILITY OF TRANSGENIC PLANT SEEDS IN UPSTREAM AND DOWNSTREAM PROCESSING

(75) Inventor: Björn Lárus Orvar, Kopavogur (IS)

(73) Assignee: ORF Liftaekni EHF., Reykjavik (IS)

( * ) Notice: Subject to any disclaimer, the term of this patent is extended or adjusted under 35 U.S.C. 154(b) by 0 days.

(21) Appl. No.: 11/659,690

(22) PCT Filed: Aug. 11, 2005

(86) PCT No.: PCT/IS2005/000017

§ 371 (c)(1),
(2), (4) Date: May 31, 2007

(87) PCT Pub. No.: WO2006/016381

PCT Pub. Date: Feb. 16, 2006

(65) Prior Publication Data

US 2008/0029003 A1    Feb. 7, 2008

(30) Foreign Application Priority Data

Aug. 11, 2004   (IS) .......................................... 7396

(51) Int. Cl.
*C12N 15/82* (2006.01)
(52) U.S. Cl. ...................... 111/200; 111/900
(58) Field of Classification Search .................. 111/200, 111/900, 915–919; 530/39.1, 324, 350, 351, 530/391.1, 328–330, 363, 308, 388.1, 323, 530/344; 536/23.1, 23.2, 23.5, 23.53, 24.2; 424/178.1; 435/69.7, 320.1, 69.1, 252.3, 435/91.1, 91.2, 7.1, 326, 325, 6, 226, 193, 435/15; 514/12, 2, 13

See application file for complete search history.

(56) References Cited

FOREIGN PATENT DOCUMENTS

| WO | WO-97/41228 A | 11/1997 |
|----|----|----|
| WO | WO-02/064803 A | 8/2002 |
| WO | WO-2006/016381 A3 | 2/2006 |

OTHER PUBLICATIONS

Kimbeng C A et al., Crop Science, Crop Science Society of America, vol. 37, No. 4 Jul. 1997, pp. 1376-1378.
Cho M-J et al., Theoretical and Applied Genetics, vol. 98, No. 8, Jun. 1999, pp. 1253-1262.
Demissi Abebe et al., Hereditas, vol. 124, No. 1, 1996, pp. 17-29.
Klein, T.M. et al.; Nature, vol. 327, pp. 70-73 (May 7, 1987).
Kasha, K.J.et al.; Euphytica, vol. 120, pp. 379-385; (2001).
Sørensen, M. B. et al.; Mol.Gen.Genet, vol. 250, pp. 750-760 (1996).
Waterhouse, P.M., et al.; Proc. Natl. Acad. Sci., vol. 95, pp. 13959-13964 (Nov. 1998).

*Primary Examiner*—Christopher J. Novosad
(74) *Attorney, Agent, or Firm*—Birch, Stewart, Kolasch & Birch, LLP (57) ABSTRACT

The present invention relates to improved methods for increasing containment and traceability of transgenic seeds, both prior to harvest and post harvest. Disclosed are methods to produce and select a desirable plant cultivar for molecular farming characterized by being easily amenable for transformation and regeneration and with visual characteristic feature such as in particular characteristic pigmentation of the seed coat or other parts of the seed that can be traced and are easily distinguished in the field or during and/or after harvesting from non-transgenic seeds of the same species that have not the visual characteristic feature.

27 Claims, 1 Drawing Sheet

TRACEABILITY OF TRANSGENIC PLANT SEEDS IN UPSTREAM AND DOWNSTREAM PROCESSING

FIELD OF THE INVENTION

The present invention is in the field of plant biotechnology and relates specifically to methods to improve containment and traceability of transgenic seeds, both prior to harvest and post harvest, through targeted breeding of desirable cultivars used for transformation.

BACKGROUND

The inherent biological capacity for protein accumulation in developing crop seeds means that many crop plants, especially monocotyledonous, have the potential to be a practical and efficient vehicle for large-scale production of heterologous recombinant proteins, e.g. high-value polypeptides for the pharmaceutical industry; a manufacturing process often referred to as molecular farming. In addition, storing heterologous polypeptides in seeds reduces down-stream processing cost since these seeds may be stored for years without affecting the quality of the heterologous polypeptide. Expression of such proteins is, preferably, under the control of seed-specific or endosperm-specific promoters.

While the biotechnology industry continues on its path of producing pharmaceuticals and industrial proteins in food and/or feed crops, such as in cereals, there is a growing concern that seeds originating from transgenic plants may accidentally make their way into the human food supply through mixing of these seeds with non-transgenic seeds during harvesting, storage or down-stream processing. This is for example emphasized by the fact that seeds from transgenic cereals produced for molecular farming are non-distinguisable from non-transgenic seeds by simple visual inspection. Therefore, there is an urgent need in molecular farming for simple technology to distinguish transgenic seeds in the field or during harvesting and downstream processing from non-transgenic seeds for safeguarding the food supply and the environment. Furthermore, there is also an urgent need to accomplish this visual tracking without adding additional genes into the streamlined expression cassettes that may be used in molecular farming for high level expression of a particular high-value heterologous protein. Such technology would be an important factor in adopting strict guidelines for improved containment of transgenic seed material intended as raw matrial for the pharmaceutical industry. This is even more important when general guidelines for Good Agricultural Practices (GAP) are set forward as a prerequisite for all molecular farming of pharmaceuticals and industrials enzymes.

Tracing transgenic material non-distinguisable from non-transgenic material by simple visual inspection, such as seeds, can be very difficult and is both time-consuming and based on tedious extraction protocols and relatively expensive diagnostic technology such as quantitative PCR and real time PCR or ELISA.

Genetic markers such as screenable markers can be used in expression vectors to screen host organisms for effective transformation, such markers include a R-locus gene which encodes a product that regulates the production of anthocyanin pigments (red color) in plant tissues (Dellaporta et al. 1988), luciferase (lux) gene which allows for bioluminescence detection or a green fluorescent protein (GFP) gene. Although they may be useful in tissue culture following gene transfer none of these however are amenable for large-scale labeling and tracking in biofarming of GM crops because of e.g. difficulties in in situ application or because of requirements for a native biochemical precursor pathway to activate the marker that may be missing in the plant of interest.

It should also be noted that conventional transformation techniques employed in plant biotechnology frequently produce "chimeric" or "mosaic" hybrid lines that originate from more than one cell, and may result in plants expressing a heterologous gene of interest introduced in the plant but not the screenable marker. Expression of screenable markers introduced by expression vectors in transformation frequently dissappears between generations and such markers may therefore be unreliable traits for visual inspection.

With increased general safety concerns relating to genetically modified crops and biofarming there is urgent need for safe and effective methods for producing genetically modified plants that are safely contained and reliably distinguishable from non-modified wild or farmed plants.

SUMMARY AND OBJECTS OF THE INVENTION

Traceability technology based on simple eye visualization or mechanized visualization of pigmentized seeds would be an immediate asset to molecular farming and plant biotechnology. It would also be highly desirable to have a simple technological approach that can help bring in much needed safeguards for genetic containment in molecular farming.

The primary objective of the present invention is summarized as providing methods for enhancing levels of biological containment and traceability of seed material in molecular farming. In a preferred embodiment of the foregoing, the primary approach is to introduce into a desirable plant host suitable for molecular farming a visual characteristic heritable trait such as characteristic pigmentation of the seed coat or other parts of the seed, and to use this new cultivar as a vehicle or host plant to produce transgenic plants expressing a heterologous protein of interest with seeds that can be traced and easily distinguished in the field or during harvesting or after harvesting from non-transgenic seeds of the same species that do not have the visual characteristic, e.g. the characteristic pigmentation of the seeds.

Typically, the plant and plant cultivar used and produced in accordance with the present Invention is selected from the group of dicotyledonous plants and monocotyledonous plants, and in preferred embodiments said plant is from the group of rape seed, soy bean, barley, maize, wheat, oat and rice. The invention is particularly useful for making and using transgenic plants such as grains that are used for expressing and accumulating a heterologous protein in the seeds of the plant. In such embodiments, it will be appreciated that not only the transgenic plants of the invention are readily recognized from non-transgenic plants but also the seeds from the transgenic plants, when separated from the plants stems, leaves, etc., are readily recognized from non-transgenic seeds, as illustrated with the particular embodiment shown in FIGS. 1 and 2.

Barley, and in particular the barley *Hordeum vulgaris* has been found by the present inventors to be particularly useful as a plant host for production of heterologous proteins of interest in transgenic plants with visually labeled seeds, as accidental cross-pollination is practically a non-existing problem.

The inventors have found rare barley cultivars that they themselves are not suitable for genetic manipulation but have very distinct visual features such that plants of said cultivars and seeds therefrom are readily and easily distinguished from common agricultural or wild cultivars.

More particularly, an object of the present invention is to apply back-cross breeding to produce new suitable host plants/cultivars for molecular farming with a visual characteristics such as in particular with pigmentized seed coat or seeds that can be easily traced through simple visualization, and, thereby, to make possible increased levels of containment.

Another object of the present invention is illustrated by an embodiment where a barley host plant selected as desirable for molecular farming is pollinated with pollen from a donor barley plant that has genetic locus or loci for pigmentized seed coat or seed, and through repeated back-crossings to produce a host plant that has all the necessary characteristics of the original plant cultivar suitable for molecular farming, including being easily amenable for tissue culture and genetic transformation, in addition to having the visual characteristic from the donor plant such as in particular pigmentized seed or seed coat that is easily recognisable visually or with automatic detection equipment.

More particularly, an object of the present invention is to provide methods to produce novel isogenic barley host plants suitable for molecular farming, including being easily amenable for tissue culture and genetic transformation, with black seeds that can be easily recognized and traced visually in the field, during harvest or after harvest. Such isogenic host plants will provide reproducibility and safety in the production of heterologous proteins, as all indovidual plants have identical double haploid genetic makeup, with essentially no variation in the seed colour.

In a preferred embodiment of the foregoing, a method of making host plant, such as in particular an isogenic barley host plant suitable for molecular farming with black seeds and being easily amenable for tissue culture and genetic transformation, comprises: (1) selecting a first barley plant from a cultivar that is easily amenable for tissue culture and genetic transformation; (2) selecting a second barley plant from a cultivar that has a colored seed coat and is not commonly used in commercial agriculture; (3) crossing the second plant with said first plant, i.e. pollinating the first plant with pollen from the plant with the colored seed coat (e.g. black, dark-grey or dark-blue or red) to generate hybrid F1 plants; (4) back-crossing the hybrid F1 plants with the cultivar that is easily amenable for tissue culture and genetic transformation; (5) repeating the back-crossing once to several times to create a hybrid cultivar line that has the colored seed coat as said second plant and retains substantially the genetic makeup of said first plant which is easily amenable for tissue culture and genetic transformation, depending on the number of back-crossings; (6) using an anther-microspore culture procedures to produce isogenic cultivar lines with the black seed coat; (7) transforming multiple such isogenic lines with a nucleic acid construct comprising an expression cassette and screen for the most suitable isogenic molecular farming line which has coloured seeds and is amenable for tissue culture and genetic transformation. Embodiments of the method include further steps of transforming such suitable isogenic molecular farming line with a nucleic acid construct encoding a plant-active promoter operably linked to a nucleotide sequence encoding a heterologous protein of interest to produce a transgenic barley line with coloured seeds expressing high-levels expression of a high-value heterologous protein.

According to the invention there is provided as an embodiment of a novel barley plant an isogenic barley cultivar for molecular farming designated herein as "Dimma".

The present invention successfully addresses the shortcomings of presently available techniques for providing adequate tracking of transgenic seeds in molecular farming, in field, during harvesting or after harvesting. In particular, the invention provides a simple solution to the problem of seed contamination where seeds originating from transgenic plants may accidentally make their way into the human or animal food supply through mixing of transgenic seeds with non-transgenic seeds during harvesting or in storage. The present invention is an economical and reliable method to reduce the risk of such seed contamination.

DETAILED DESCRIPTION OF THE PRESENT INVENTION

Herein below, preferred embodiments of the present invention will be described in detail.

Unless defined otherwise, all technical and scientific terms used herein have the same meaning as is commonly understood and used by one of skill in the art to which this invention belongs.

The term "molecular farming" used herein refers to the process of using plants of any kind in open fields or in closed facility to produce valuable biological compounds such as proteins for further processing.

The term "protein" is used herein interchangeably with the terms "polypeptide" and "peptide".

The term "seed contamination" refers to when seeds from plants, such as cereals, used for molecular farming are accidentally mixed with seeds from plants used for food or feed production. The term "containment" or "containment of transgenic seeds" refers to when seeds from transgenic plant cultivars are successfully kept separated from non-transgenic seeds and are not mixed with non-transgenic seeds, either in the field, during harvesting or after harvesting.

The term "plant cultivar" refers to a plant of a kind originating and persistent under cultivation that may be produced by selective hybridization or can be found in wild populations and is maintained by vegetative propagation or by inbred seed.

The term "desirable parent cultivar" or "desirable cultivar" used herein refers to a plant cultivar selected to be modified through breeding to become a suitable host cultivar for molecular farming. The term "host cultivar" refers to the cultivar that is genetically transformed to be used as a plant cultivar for production of recombinant proteins in molecular farming.

The terms "F₁ generation" or "F₁ plants" or "F₁ hybrid" used herein refer to the first generation produced in crossing between a desirable cultivar and a cultivar with a desired trait, such as characteristic pigmentation patterns in seed or seed coat.

The term "back-crossing" refers to the process in which the breeder repeatedly crosses the hybrid progeny (F₁ to F₁₊ₙ where n is 1 or larger than 1) back to the initial desirable parent cultivar. A non-limiting example is when a hybrid progeny between Hordeum vulgaris cv. "Golden Promise" (the desirable parent cultivar) and Hordeum vulgaris cv. "Svarthovdi" (cultivar with a desirable trait) is repeatedly crossed back with the initial desirable parent cultivar "Golden Promise".

The term "isogenic line" or "isogenic barley" used herein refers to a diploid barley cultivar or line that is a double haploid line or homozygous for more or less every allele.

Figure 1:
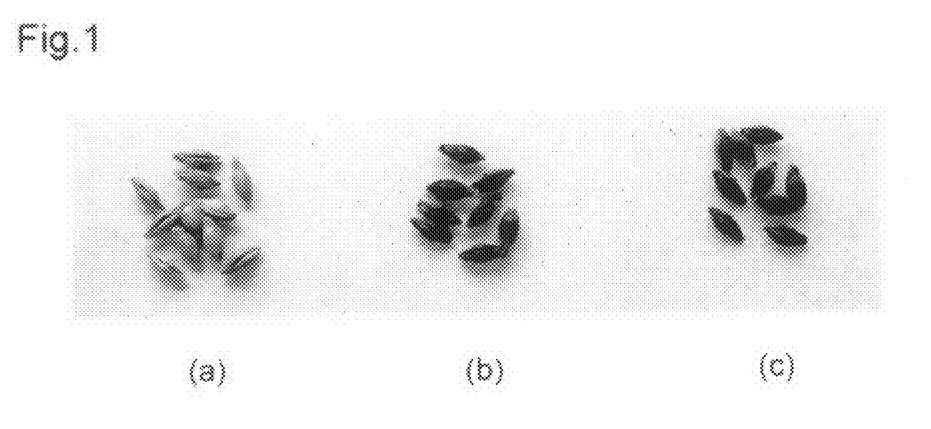
FIG. 1 Fully developed seed from the barley cultivar "Golden Promise" (a), "Svarthovdi" (b) and the isogenic barley hybrid line "Dimma" (c).
Figure 2:
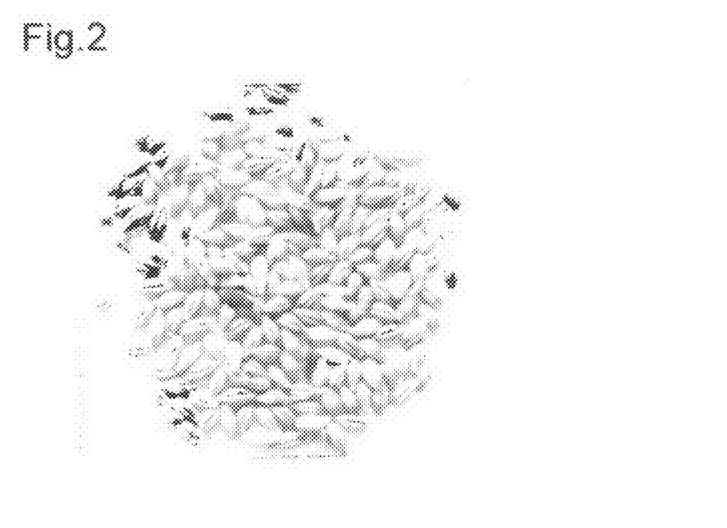
FIG. 2 illustrates the visual difference of the "Dimma" seeds in a mixture of seeds of "Dimma" and the cultivar "Golden Promise".

The term "seed pigmentation" refers to accumulation of pigment compounds produced by the plant cells in the seed or seed coat. The term "characteristic pigmentation" refers to pigmentation patterns in the seed or seed coat that are easily distinguised from pigmentation patterns that commercial or common cultivars may have. As a non-limiting example of pigmentation patterns in a commercial cultivar is the pigmentation pattern seen in the cultivar Hordeum vulgaris cv. "Golden Promise" (FIG. 1a). As a non-limiting example of charateristic pigmentation pattern is the pigmentation pattern seen in the Hordeum vulgaris cv. "Svarthovdi" (FIG. 1b). "Seed coat" or "testa" refers to the outer and inner integument of a seed, including the pigment layer, or the protective outer layer of the seed. As a non-limiting example black melanin-like pigment accumulation in the seeds of the barley cultivar "Svarthovdi" is according to the present invention.

The term "mechanised detection equipment" or "automatic detection equipment" is any tool or instrument capable of distinguishing between seeds that are pigmentized and seeds that are not. The term "visual tracking" refers to any means of tracking and identifying seeds based on their pigmentation or pigmentation patterns of seed coat or any other parts of the seed. Such detection equipment can be based on spectrophotometric techniques for measuring absorbance and/or reflectance of sample seeds passed through light beam path between a light source and detector. Machine vision cameras with CCD or CMOS detector connected with computer equipment programmed with suitable pattern recognition software is also applicable for automatic detection of visually labelled seeds according to the invention.

The term "coding sequence" refers to a nucleotide sequence that codes for a specific amino acid sequence.

A "promoter" is defined as an array of one or more nucleic acid control sequences or transcription regulator binding sites that direct transcription of an operably linked nucleic acid.

The term "transformation" or "genetic transformation" refers to the transfer of a nucleic acid molecule into the genome of a host organism, resulting in genetically stable inheritance. Host organisms containing the transformed nucleic acid fragments are referred to as "transgenic" organisms. A "transgenic plant host cell" of the invention contains at least one foreign, preferably two foreign nucleic acid molecule(s) stably integrated in the genome. Examples of methods of plant transformation include Agrobacterium-mediated transformation (De Blaere et al. 1987) and particle-bombardment or "gene gun" transformation technology (Klein et al. (1987); U.S. Pat. No. 4,945,050).

The term "selectable marker" or "selectable marker gene" refers to a gene that imparts a distinct phenotypic trait to the cell or an organism expressing that gene characterized by that cell or organism being more tolerant to the toxicity of a particular chemical agent such as herbicide or antibiotic or the like.

The term "screenable marker" refers to a phenotypic trait of a cell or an organism that can be detected through observation or testing, typically through visual inspection.

After selecting a desirable plant cultivar for molecular farming that is easily amenable for tissue culture and genetic transformation, another cultivar is selected that have seeds that can be easily distinguished visually from the seeds from the desirable cultivar. These seeds can have different colour or pigmentation, such as the black seeds of some local Ethiopian barley cultivars, or a blue, red or grey colour or colour patterns, or have other morphological features that are easily distinguished visually from seeds from cultivars used for food or feed. It is preferred that the genetic locus or loci responsible for the characteristic feature, such as the black seed coat of some local Ethiopian barley cultivars, is a dominant, highly heritable trait with strong penetrance. A number of different barley cultivars with highly heritable traits causing pigmentized seeds have been described in the literature. The desirable cultivar for molecular farming is crossed manually with the cultivar with the desirable trait for pigmentized seed or seed coat, and the hybrid progeny back-crossed repeatedly with the desirable cultivar. After a few back-crossings (e.g. 2, 3, 4 or more) the hybrid is tested for it's amenability for tissue culture and genetic transformation and compared with the initial desirable cultivar. Once the amenability for tissue culture and genetic transformation of the hybrid line is deemed sufficient and comparable with the desirable cultivar, the hybrid line is used to produce a double haploid line or isogenic line such as preferably by using the anther-microspore culture procedures as described in Example 2 and has been described in detail by Kasha et al. (1992; 2001) to produce a line from this hybrid cultivar line that is homozygous for the desirable trait of pigmentized seeds. This isogenic hybrid line can then be used as the host cultivar for molecular farming.

In preferred embodiments, a plurality of isogenic plants are obtained from the hybrid line obtained after back-crossing; the different isogenic genetic makeup of the individual isogenic lines represent a large number of the possible resultant crossings of the F3 descendants; seeds of said isogenic plants are sown and grown and subsequently tested for amenability for transformation and tissue culture, by transforming with an expression vector such as described herein and screening for efficient transformation and expression; and based on said testing an isogenic line is selected from said plurality of isogenic plants as the transformable plant for production of a heterologous protein of interest.

Monocotyledonous and dicotyledonous plants that can be genetically manipulated can be used as the desirable cultivar in the present invention. Preferably the plant is a monocotyledonous, more preferably barley, and most preferably the barley Hordeum vulgaris. A plant that can be genetically transformed is a plant into which heterologous DNA sequence, including DNA sequence for a coding region, can be introduced, expressed, stably maintained, and transmitted to subsequent generations of progeny. Genetic manipulation and transformation methods have been used to produce barley plants that are using herbicide resistance including, for instance, bialaphos or basta, or antibiotic resistance, such as hygromycin resistance, as a selectable marker.

It is preferred that the promoters utilized in the DNA construct of the present invention have strong activity in the visually distinguisable plant part such as in the seed tissues where the accumulation of the heterologous polypeptide of interest is desired. Such promoters may be obtained from a variety of plant genetic material or from plant viruses. It is preferred that the particular promoter selected is suitable for expression of heterologous protein in monocotyledonous seeds, more preferably in barley, and most preferably in the endosperm tissue of the seed.

The recombinant plasmid of the invention can be obtained by ligating (inserting) the DNA sequences of interest into an appropriate plasmid that is replicable in a bacterial host. The DNA sequences, such as the gene encoding the heterologous protein of interest or the DNA promoter sequences designed for tissue specific seed expression should be operably Incorporated into the plasmid that may contain, in addition to a promoter and for this purpose, and if desired, additional enhancer DNA sequences, scaffold-attachment regions, introns, poly(A) addition signal, ribosome binding sequence and selectable marker gene of interest such as hygromycin resistance gene, ampicillin resistance gene, bialaphos resistance gene, or the like. Such a selectable marker is preferred in the transformation of Barley plants as the transformation efficiency is relatively low and therefore it is desirable to be able to select positive transformed cells from non-transformed cells.

EXAMPLES

The following examples are provided to better define the present invention and to guide those of ordinary skill in the art in the practice of the present invention. Unless otherwise noted, terms are to be understood according to conventional usage by those of ordinary skill In the relevant art.

METHODS

Artificial Pollination of Barley Lines in Crossing and Back-Crossing

*Hordeum vulgaris* or barley is a self-fertilizing plant meaning that pollen from one flower usually pollinates an ovule in the same flower. With cultivation self-pollination will eventually lead to isogenic or near isogenic lines, meaning that most or all alleles are homozygous. To introduce a new trait or phenotype into such self-fertilizing species artificial pollination, or crossing, is necessary. Artificial pollination, or crossing, in barley is carried out in greenhouses. In the beginning two cultivars, with some desirable traits, are selected and their seeds planted in pots. The sowing is repeated over a few days to secure that the developmental stage of the parents selected for the crossing is compatible. The artificial pollination is carried out in two steps. The first step is When the flowers on the host cultivar are just fully developed, or just after the tillers below the spikes start to emerge from the leaf sheath. Each flower or spikelet on the spike is then opened and the three stamens inside the flower removed with forceps. Each spike treated is then bagged to hinder pollen spread to the spikelets and to hinder flower desiccation. The second step is the actual artificial pollination or crossing and takes place three to five days after the removal of the stamens, or when the carpel is fully developed in the host cultivar and ready to be pollinated. Stamens in the donor cultivar that have not already dispersed their pollen on their own carpel and are fully developed are selected and used to pollinate the host spikelets with removed stamens. The success rate of the artificial pollination is usually between 50% and 70%.

Production of Double-Haploid, Isogenic Barley Hybrid Lines

The technique is based on the protocol developed by Kasha et al. (2001). Seeds are sowed on a mixture of 75% light sphagnum peat and 25% pumice (medium grain size) and plants grown at 16° C. daytime (16 hours) and 12° C. nighttime (8 hours) and 70% relative humidity under 250 µmol $m^{-2}$ $s^{-1}$ of continuous light during daytime in cool-white fluorescent and sub-irrigated as needed with water. Under these conditions the plants grow vegetatively for about 55-95 days until the immature spikes can be collected at the appropriate stage. The ideal stage for culturing microspores is at the mid to late-uninucleate stage. After collection the spikes are laid on a cheese cloth and sprayed well with 80% EtOH, covered with the cheesecloth and dried for 5 minutes. The spikes are removed from the sheath and placed in a sterile Petri plates, about 10 spikes into each plate. 15 ml of ice-cold, 0.3 M mannitol are added to each plate which are then sealed with transparent plastic wrap, covered with aluminium foil and stored at 4° C. for 3-4 days. The ends are then cut off the pre-treated spikes and throw away and the spikes cut into 1-2 cm pieces into a chilled blender cup with ice-cold mannitol. The ingredients are blended at low speed in Waring blender for 5 sec and the slurry filtered through 500µ+200µ nylon membranes. The filtrate is collected, filtered through 100p membrane and collected in 50 ml BD Falcon tubes. The tubes are spun for 5 min, the fluid poured carefully off and wash with 0.3 M mannitol, combine in one or two 50 ml tubes and spun for 5 min, the fluid poured off from the 50 ml tube, the pellet re-suspended in 2 ml mannitol and pipetted onto ca 12 ml of 20% maltose in 15 ml Falcon tubes. The tubes are spun for 5 min, the live microspores collected with a pipette from a layer above the middle of the tube, re-suspended in mannitol and spun for 5 min and the microspore pellet re-suspended in 2 ml FHG media. The microspore suspension is then pipetted gently on a pre-wetted filter paper in a porcelain funnel under vacuum. The top-most filter paper is transferred onto the center of an FHG-solidified media in a Petri dish and the plates sealed with plastic wrap and incubated in the dark at 25° C. for 3-4 weeks. After 7-10 days fresh liquid FHG is added to the plates. The embryo-like structures are transferred into MS differentiation media when they reach 1-2 mm in size, incubated in the dark for 3 days and then transferred to 8 hour light at 22° C. for a few weeks. Small plantlets (3-4 cm) are transferred into MS regeneration media in boxes and plants transplanted as soon as roots are well developed.

Evaluation of Amenability for Tissue Culture and Genetic Transformation in Barley Hybrid Lines a) Plant Material for Genetic Transformation

*Hordeum vulgaris* cv Golden Promise seeds and seeds from different hybrid lines are sowed on a mixture of 75% light sphagnum peat and 25% pumice (medium grain size) and plants grown at 16° C. daytime (16 hours) and 12° C. nighttime (8 hours) and 70% relative humidity under 250 µmol $m^{-2}$ $s^{-1}$ of continuous light during daytime in cool-white fluorescent and sub-irrigated as needed with water. Under these conditions the plants grow vegetatively for about 55-95 days or until immature seeds are ready as material for transformation, which is about 8 to 14 days post anthesis. Seeds are sterilized in 3% sodium hypochlorite for 40 min in rotary shaker and rinsed with five changes of sterile water.

b) Bacterial Strains and Preparation for Plant Transformation

*Agrobacterium tumefaciens*, harbouring a binary vector in trans with a Ti-plasmid possessing a vir region, is used to introduce into barley the T-DNA region with the DNA construct regulating the expression of the heterologous protein of interest. Transformation of both *E.coli* XL-Blue and *Agrobacterium tumefaciens* bacteria is done by electroporation as described by Maniatis et al., Molecular Cloning: A Laboratory Manual, Cold Spring Harbor Laboratory Press, Cold Spring Harbor, N.Y. (1982). For preparation for transformation of plant a single colony of the *Agrobacterium* culture is inoculated 5 ml of Agro medium (Tryptone 5 g/L, yeast extract 2.5 g/L, mannitol 5 g/L, glutamic acid 1 g/L, $KH_2PO_4$ 250 mg/L, $MgSO_s$-$7H_2O$ 100 mg/L, biotin 1 µg/L, pH 7.0, 25 µg/ml rifampicin, 50 µg/ml spectinomycin) and grown for 24 to 40 hours at 27° C. In sterile eppendorf tubes 200 µl of culture is added to 200 µl of 30% aqueous glycerol (previously sterillsed) and culture vortexed well and left on the bench for 2 hours before stored at −80° C. For each transformation one tube is removed from the −80° C. freezer, thawed and approx. 200 µl of *Agrobacterium* bacterial stock added to 5 ml Agro medium without antibiotic. The culture is then grown for 17 to 20 hours at 27° C. before being used for inoculation of plant material (see below).

c) Preparation of Barley Explants for *Agrobacterium*-Induced Transformation

On day one approximately 10 barley heads are picked, approx. 8 to 14 days after anthesis, awns and seeds removed and embryos between 1.5 mm and 2 mm in size selected. The initial plant material needs to be healthy and mature, and not waterlogged, and the seeds should be green with no signs of disease or fungi. Seeds are placed in 50 ml falcon tube (no more than half full) and rinsed with 70% ethanol and ethanol then poured off. $^{20}$% bleach solution (White King) Is then added and mixed for 20 minutes. In laminar airflow hood the bleach solution is poured off, the seeds rinsed with sterile water (about 5-8 rinses) and tube placed at 4° C. O/N. On day two seeds are placed in a sterile Petri dish on the microscope platform. The position of the embryo is located, the end cut off the seed and a cut down the side of seed made. The seed is then held firmly with forceps and the middle of the seed pressured so that the embryo pops out. The embryo is held in place with forceps and scalpel blade inserted in the groove between the scutellum and axis and the axis slowly excised. The embryo minus the axis is placed on a regeneration media, cut side up, in centre of Petri dish with approximately 25 embryos to a plate. For each transformation a total of 200 embryos are used.

d) Handling of Binary Vector

The binary vector is propagated in *E. coil* XI-Blue LB culture medium containing 100 µg/ml spectinomycin at 37° C. and the vector subsequently purified from 100 ml culture grown overnight using the QIAGEN® Plasmid Midi Kit. The purified binary vector is introduced into the *Agrobacterium tumefaciens* with electroporation by placing 1 µl (1 µg) of the vector in sterile cuvette with 0.1 cm gap (BioRad), washing down the vector with 40 µl of electrocompetent cells, and setting the voltage at 2.5 kV and capacitance at 21 µF for the electroporation. The cells are spread on YEP selection plates containing 100 µg/ml spectinomycin and 20 µg/ml rifampicin grown at 28° C. for 2 days. Plasmid restriction digest analysis from *A. tumefaciens* transformants is carried out to verify the intactness of the binary vector.

e) *Agrobacterium* Infection of Barley Explants

Approximately 10 µl of *Agrobacterium* culture is pipetted onto each embryo ensuring all embryos come in contact with the solution. The embryos were flipped (cut side down) and dragged across the regeneration media to the outside of plate, removing excess *Agrobacterium*. The embryos are then transferred to fresh regeneration media plates (cut side up) at evenly spaced intervals (25 per plate) and placed in dark cabinet at 24° C. Regeneration and organogenesis in barley tissue culture after *Agrobacterium* infection After three days the embryos are transferred to a fresh regeneration media with a selectable marker, such as bialaphos or hygromycin and left there for four to six weeks, subculturing every two weeks. To regenerate shoots, the calli are transferred to shoot-induction media (SIM) and surviving callus and regenerating shoots transferred to fresh SIM every two weeks untils small plantlets are formed. Then the plantlets are transferred to root-induction media (RIM), surviving plants counted and then potted in soil. After one month in soil leaf explant is colected from each plant for PCR screening of the transgene and the number of transgenic plants per 100 embryos inoculated with *Agrobacterium* calculated.

DNA Extraction and PCR Analysis of Transgenic Lines

Genomic DNA for PCR amplification is extracted from ca 200 mg young leaf tissue using the NudeoSpin Plant Kit® from Clonetech, and according to manufacturer's instructions. PCR amplifications for the hygromycin phosphotransferase gene (hph) are performed in 25 µl reaction mixture (50 mM KCl, 10 mM Tris-HCl (pH 8.4), 1.5 mM $MgCL_2$, 200 µM of each dNTP, about 0.25 µM primer, 2.5 U Taq polymerase (Fermentas) and 50 ng to 100 ng template DNA. The PCR reaction is carried first out with 3 minute at 94° C., and then 31 cycles with the following steps: 30 seconds at 66° C., 45 seconds at 72° C., 30 seconds at 94° C. The amplification reaction is ended with a 4 min extension step at 72° C. Two hph specific primers (hph129 and hph130) are used for amplification. The sequence of the primers are the following: hph129, 5'-CGGGCGCCATGAAAAAGCCTGAACTCAC-CGCGACG-3' (SEQ ID NO: 1); hph130, 5'-CGGGCGC-CCTATTCCTTTGCCCTCGGACGAGTGC-3' (SEQ ID NO: 2).

Example 1

Breeding of Transformable Barley Hybrid Line with Black Seeds

Seeds from *Hordeum vulgaris* cv Golden Promise which is amenable for plant transformation and plant regeneration through tissue culture were planted in pots. Sowing was repeated over a few days and plants grown in greenhouse under natural light. At the same time seeds from a *Hordeum vulgaris* cultivar referred to as "Svarthovdi" that has black seeds but is not amenable for plant transformation and plant regeneration through tissue culture were potted and grown under same conditions. The black seed is a dominant trait of "Svarthofdi" and the phenotype manifested in the seed coat or the aleuron layer of the seed. When the seed is fully mature at least 50% of the seed coat has the black pigmentation. When the flowers on the Golden Promise cultivar were just fully developed, or just after the tillers below the spikes start to emerge from the leaf sheath, ten flowers or spikelet on the spike were opened and the three stamens inside the flowers removed with forceps. Each spike treated was then bagged to hinder pollen spread to the spikelets and flower desiccation. Four days later fully developed stames from cultivar "Svarthovdi" were collected and used to pollinate the carpel of the ten flowers of the Golden Promise cultivar with stamens removed.

Following pollination the spikes were kept bagged and the seeds not harvested until fully developed. The F1 embryos in these seeds are all heterozygous for the black allele. The genetic background is 50% Golden Promise and 50% "Svarthovdi" with the black pigmentized seed coat since the black allele is dominant. All treated F1 seeds were sowed in pots and the F1 plants grown until spikelets were ready for back-crossing with pollen from cultivar Golden Promise. The back-crossing with Golden Promise was carried out as described above and the F2 seeds sowed in pots and the F2 plants grown under greenhouse conditions until spikelets were ready for repeating the back-crossing with pollen from cultivar Golden Promise. The genetic background in F2 plants is calculated as 75% cv Golden Promise and 25% cv "Svarthovdi". The F2 plants were grown in greenhouse until spikelets where ready for repeating the back-crossing with pollen from cultivar Golden Promise as described above. The genetic background in F3 plants should be 87.5% cv Golden Promise and 12.5% cv "Svarthovdi". The F3 spikelets were allowed to self-pollinate and to develop to fully mature F3 seeds. 75% of the F3 seeds had the black phenotype and 25% had the traditional yellow seed phenotype. Black F3 seeds were collected and sowed in pots and the F3 plants grown under greenhouse conditions until the microspores were ready for harvesting for microspore culture to produce double-haploid isogenic hybrid lines homozygous for either the black seed phenotype or yellow seed phenotype, all having a genetic background which is predominantly (calculated 87,5%) from the Golden Promise cultivar which is amenable for plant transformation and plant regeneration. The isogenic hybrid lines where grown to maturity and lines with the black seeds phenotype collected for testing amenability for plant transformation and plant regeneration.

Example 2

Figure 3:
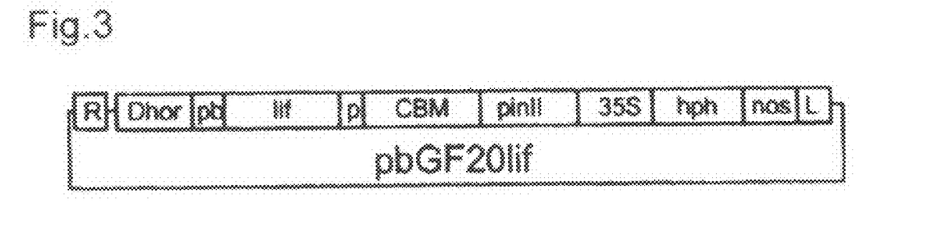
FIG. 3 illustrates a schematic representation of the expression cassette pbGF20lif used for transformation and selection of "Dimma" in accordance with the present invention. Abbreviations: Dhor, endosperm-specific D-hordein promoter; pb, signal peptide; lif, leukemia inhibitory factor cDNA sequence; p, linker; CBM, carbohydrate binding module cDNA; pinII, potato proteinase inhibitor II gene termination signal; 35S, cauliflower mosaic virus 35S promoter; hph, hygromycin phosphotransferase from *E. coli* (Genebank accession #K01193); nos, nopaline synthase termination signal; R, right border; L, left border.

Selection of Barley Hybrid Line with Black Seeds and Amenable for Plant Transformation and Plant Regeneration Through Tissue Culture Using Genetic Transformation Immature seeds of 50 hybrid double haploid isogenic lines, about 8 to 14 days post anthesis, were harvested and stored overnight at 4° C. in dark. The cold-incubated immature seed was treated in 70% EtOH for 1 min. and then for 10 min. In 0.6% sodium hypochlorite, followed by thorough washing (5 -8 times) in sterile distilled water an placed on a sterile Petri plate under dissecting microscope in a laminar flow hood under sterile conditions. The position of the embryo is located, the end of the seed cut off and a scission made down the side of the seed. The seed was held down with forceps and the middle of the seed pressed down so that the embryo was squeezed out. The embryo was held in place with the forceps, scalpel blade inserted in the groove between scutellum and axis and the axis slowly excised. The scutellum was placed on callus induction media, the cut side up, and inoculated with 25 µl to 40 µl of full-strength *Agrobacterium tumefaciens* carrying the plant transformation vector pbGF20lif (SEQ ID NO: 3, see FIG. 3 and the above description thereof) for 1 to 5 minutes. After inoculation the scutellum was dragged to the outside of the dish to lower the bacterial load and to reduce the overgrowth during the co-cultivation phase. The infected scutellum was transferred to a new callus induction media plate and the plate incubated at 24° C. in dark for 3 days. After 3 days the scutellum was transferred to new callus induction media but with 100 µg/ml timentin for killing off the *Agrobacterium* and 50 µg/ml hygromycin for selecting transformed cells and incubated for 4 weeks in dark at 24° C., subculturing after 2 weeks. The callus was then transferred to shoot induction media Including 2.5 mg/L BAP, 50 µg/ml timentin and 25 µg/ml hygromycin, and incubated in high light for 4 to 10 weeks. Individual regenerating plantlets were transferred to rooting medium (50 µg/ml timentin and 25 µg/ml hygromycin and without hormones). After development to approx. 5 to 7 cm shoots with roots, transgenic plants were moved to soil and grown there under full light. Seeds from transgenic lines were screened for expression of lif-cbm heterologous fusion protein using ELISA with polydonal antibody raised against cbm (cellulose binding module) in rabbit. The hybrid double haploid isogenic line that gave the highest percentage of transgenic plants, was selected as the most suitable line for molecular farming and referred to "Dimma".

Example 3

Production of a Heterologous Protein of Interest

Seeds from the plant line selected in Example 2 and referred to as Dimma are transformed essentially as described above, except that a gene encoding for a heterologous protein of interest is introduced into the expression vector, instead of the lif-cbm encoding sequence. Successful transformants are sown and grown; seeds are collected and the protein of interest extracted therefrom. It is particularly preferred to express the heterologous protein of interest as a cbm fusion protein, as such fusion proteins can be readily extracted and purified on a large scale and the cbm portion of the fusion protein can optionally be readily cleaved of and separated from the heterologous protein of interest, by introducing a cleaving site recognized by a suitable protease between the cbm encoding sequence and sequence encoding the heterologous protein of interest. Such methods are described in detail in applicant's co-pending applications WO 2005/021762 and WO 2005/021764 which are incorporated herein in full by reference.

Although only preferred embodiments of the invention are specifically illustrated, numerous modifications and variations in the invention as described in the above examples are expected to occur to those skilled in the art, without departing from the spirit and intended scope of the invention.

References Cited

Davis et al., 1994: In: Basic Methods in Molecular Bioogy. Norwalk. Connecticut: Appelton and Lenge:350-355.
De Blaere et al. (1987) Meth. Enzymol. 143:277
Kasha et al. (1992): In: Barley Genetics VI, vol. 2 Proc. 6th Int. Barley Genet. Symp. pp 793-806. Munksgaard Int. Publ. Copenhagen.
Kasha et al. (2001) Euphytica 120:379-385.
Klein et al. (1987) Nature 327:70-73
Maniatis et al. (1982) Molecular Cloning: A Laboratory Manual, Cold Spring Harbor Laboratory Press, Cold Spring Harbor, N.Y.
Sanford et al. U.S. Pat. No. 4,945,050
Sörensen et al. (1996) Mol. Gen, Genet. 250:750-760
Waterhouse et al. (1998) Proc. Natl. Acad. Sci. 95:13959-13964

The invention claimed is:

1. A process for producing a transformable plant for use in molecular farming with traceable seeds having a visual characteristic feature, comprising the steps of:
(a) providing a desirable first cultivar for expression and accumulation of a heterologous protein in its seeds or any part thereof, wherein said cultivar is amenable for plant transformation and plant regeneration through tissue culture, and
(b) providing a second cultivar with seeds that have a visual characteristic feature such that seeds of said cultivar are visually substantially different from the seeds of common agricultural or wild cultivars of the same species that grow in the geographic region intended for growing said transformed plant,
(c) crossing said second cultivar with said first cultivar to yield a hybrid line,
(d) back-crossing said hybrid line with said first cultivar to obtain hybrid plants, the genome of which are substantially comprised of the genome of said first cultivar, and have seeds with the same visual characteristic feature as seeds in said second cultivar,
(e) selecting from said hybrid plants a host hybrid line which retains the characteristics of said first cultivar making it amenable for plant transformation and plant regeneration.

2. The process of claim 1 wherein said visual characteristic feature is a substantially different seed colour than the seed colour of said common agricultural or wild cultivars of the same species that grow in the geographic region intended for growing said transformed plant.

3. The process of claim 2 wherein at least 50% of the surface of said visibly labelled seeds of said genetically transformed plant have substantially different colour from the seed colour of common agricultural or wild cultivars of the same species that grow in the geographic region intended for growing said transformed plant.

4. The process of claim 1 wherein said genetically transformed plant is a monocotyledonous plant.

5. The process of claim 4 wherein said genetically transformed plant is barley.

6. The process of claim 1 wherein the back-crossing step (d) is repeated at least once to obtain said hybrid plants.

7. The process of claim 6, wherein the back-crossing step (d) is repeated at least twice to obtain said hybrid plants.

8. The process of claim 1, wherein microspores from the said hybrid plants are used for tissue culture to yield isogenic hybrid lines amenable for plant transformation and plant regeneration with seeds having said different colour.

9. The process of claim 8, wherein a plurality of said isogenic hybrid plants are transformed with a nucleic acid construct comprising a selectable marker gene operably linked to a promoter, and wherein said host hybrid line is selected based on evaluating the efficiency of transformation and expression of a gene product of said nucleic acid construct.

10. The process of claim 1, further comprising the steps of:
(f) providing a nucleic acid construct that comprises a nucleic acid sequence encoding a plant-active promoter operably linked to a nucleotide sequence encoding a heterologous protein of interest,
(g) transforming one or more cells from said host hybrid line with said nucleic acid construct,
(h) regenerating a plant from said transformed one or more plant host cells from said host hybrid line, and growing said plant to obtain a genetically transformed plant with visibly labeled seeds expressing said heterologous protein.

11. The process of claim 10 wherein said promoter is a seed-specific promoter.

12. The process of claim 10 wherein said heterologous protein of interest is selected from the group consisting of collagens, collagenase, homeobox polypeptides, monoclonal antibodies, secreted antibodies, antibody singe chains including light chains and heavy chains, manno se-binding lectin, pepsin, chymotrypsin, trypsin, casein, human growth hormone, human serum albumin, human insulin, cellulases, pectinases, hemicellulases, phytases, hydrolases, peroxidases, fibrinogen, factor LX, factor XIII, thrombin, protein C, xylanase, isoamylase, glucoamylase, amylases, lysozyme, beta.-glucanase, glucocerebrosidase, caseins, lactase, urease, glucose isomerase, invertase, streptavidin, esterases, alkaline phosphatase, protease inhibitors, pepsin, chymotrypsin, trypsin, papain, kinases, phosphatases, deoxyribonucleases, ribonucleases, phosphlipases, lipases, laccase, spider silk proteins, antifreeze proteins, antimicrobial peptides or defensins, growth factors and cytokinins.

13. The process of claim 10 wherein said heterologous protein of interest is leukemia inhibitory factor.

14. The process of claim 10 wherein said nucleic acid construct comprises a nucleic acid sequence encoding a cellulose binding module (cbm) adjacent to the nucleic acid sequence encoding said heterdogous protein of interest, optionally intercepted by a nucleic acid sequence encoding a proteolytic cleavage site.

15. The process of claim 10 wherein said genetically transformed plant with said visibly labelled seeds is grown under conditions whereby said nucleic acid sequence encoding said heteroingus protein of interest is expressed such that said protein is accumulated in the seeds of said plant.

16. A transgenic barley plant expressing in its seeds a heterologous protein of interest, producing in its seeds or seed coat a pigment that is substantially visibly different from the natural yellow seed colour of conventional barley such as the barley species *Hordeum vulgaris* which is produced by the process of claim 10.

17. The process of claim 1, wherein said plant is transformable with *agrobacterium*.

18. A transgenic barley plant expressing in its seeds a heterologous protein of interest, producing in its seeds or seed coat a pigment that is substantially visibly different from the natural yellow seed colour of conventional barley such as the barley species *Hordeum vulgaris*.

19. The transgenic barley plant of claim 18 producing black, red or blue pigment sufficient to give the seeds of the plant a noticeable blue, red, grey or black color.

20. The transgenic barley plant of claim 18 expressing substantially all of said heterologous protein in its seeds.

21. The transgenic barley plant of claim 18 having in its genome a seed-specific promoter operably linked to the nucleic acid sequence encoding said heterologous protein.

22. The transgenic barley plant of claim 21 wherein said seed-specific promoter is selected from the group consisting of promoters from monocotyledonous plant that are primarily seed-specific.

23. The transgenic barley plant of claim 18, which plant is isogenic.

24. The transgenic barley plant of claim 18 being amenable to tissue culture and genetic transformation.

25. The transgenic barley plant of claim 18, wherein said heterologous protein is expressed as a fusion protein comprising a carbohydrate binding module.

26. A process for producing a heterologous protein of interest comprising:
   (a) growing a tranagenic barley plant according to claim 18, which plant has visibly different seeds from common agricultural or wild cultivars of the same species that grow in the geographic region said transgenic barley plant expressing in its seeds said heterologous protein of interest,
   (b) harvesting said plant and
   (c) extracting from its seeds said heterologous protein.

27. The process of claim 26 wherein a plurality of said transgenic barley plants are grown in an outdoor field, separated from any non-transgenic barley plants.

* * * * *

SEQUENCE LISTING

```
<160> NUMBER OF SEQ ID NOS: 3

<210> SEQ ID NO 1
<211> LENGTH: 35
<212> TYPE: DNA
<213> ORGANISM: Artificial Sequence
<220> FEATURE:
```

```
<223> OTHER INFORMATION: Hygromycin Phosphotransferase Gene (hph)
      specific synthetic DNA primer - hph129

<400> SEQUENCE: 1
cgggcgccat gaaaaagcct gaactcaccg cgacg                              35

<210> SEQ ID NO 2
<211> LENGTH: 34
<212> TYPE: DNA
<213> ORGANISM: Artificial Sequence
<220> FEATURE:
<223> OTHER INFORMATION: Hygromycin Phosphotransferase Gene (hph)
      specific synthetic DNA primer - hph130

<400> SEQUENCE: 2
cgggcgccct attcctttgc cctcggacga gtgc                               34

<210> SEQ ID NO 3
<211> LENGTH: 4313
<212> TYPE: DNA
<213> ORGANISM: Artificial Sequence
<220> FEATURE:
<223> OTHER INFORMATION: expression vector- plant transformation vector
      pbGF201if

<400> SEQUENCE: 3 gaattcccctt cgagtgcccg ccgatttgcc agcaatggct aacagacaca tattctgcca    60 aaacccccaga acaataatca cttctcgtag atgaagagaa cagaccaaga tacaaacgtc   120
cacgcttcag caaacagtac cccagaacta ggattaagcc gattacgcgg ctttagcaga   180
ccgtccaaaa aaactgtttt gcaaagctcc aattcctcct tgcttatcca atttcttttg   240
tgttggcaaa ctgcacttgt ccaaccgatt ttgttcttcc cgtgtttctt cttaggctaa   300
ctaacacagc cgtgcacata gccatggtcc ggaatcttca cctcgtccct ataaaagccc   360
agccaatctc cacaatctca tcatcaccga gaacaccgag aaccacaaaa ctagagatca   420
attcattgac agtccaccga gatggctaag cggctggtcc tctttgtggc ggtaatcgtc   480
gccctcgtgg ctctcaccac cgctgaacgt cccatggtgg ccaccgccaa gtacggcacc   540
ccagtgatcg acggggagat cgacgagatc tggaacacca ccgaggagat cgagaccaag   600
gccgtggccg tggggagcct cgacaagaac gccaccgcca aggtgcgcgt gctctgggac   660
gagaactacc tctacgtgct cgccatcgtg aaggacccag tgctcaacaa ggacaacagc   720 aaccccttggg agcaagacag cgtggagatc ttcatcgacg agaacaacca caagaccggc   780
tactacgagg acgacgacgc ccaattccgc gtgaactaca tgaacgagca aaccttcggg   840
accggcggga gccagcccg cttcaagacc gccgtgaagc tcatcgaggg gggctacatc   900
gtggaggccg ccatcaagtg aagaccatc aagccaaccc caaacaccgt gatcggcttc   960
aacatccaag tgaacgacgc caacgagaag gggcaacgcg tggggatcat cagctggagc  1020
gacccaacca acaacagctg gcgcgaccca agcaagttcg ggaacctccg cctcatcaag  1080
ccaaccccaa cccattgta caccgacgac gacgacaagt ccccactccc aatcaccccca  1140 gtgaacgcca cctgcgccat caggcaccca tgccacggca acctcatgaa ccagatcaag  1200
aaccagctcg cccagctcaa cggctccgcc aacgccctct catctcctaa ctacaccgcc  1260
cagggcgagc cattcccaaa caacgtggag aagtctctgc gccccaaacat gaccgacttc  1320 ccatcccttcc acggcaacgg caccgaaaag accaagctcg tggagctgta ccgcatggtg  1380
gcctacctct ccgcctcccct caccaacatc accagggacc agaaggtgct caaccccaacc  1440
```

-continued

```
gccgtgtccc tccaggtgaa gctcaacgcc accatcgacg tgatgagggg cctcctctcc    1500
aacgtgctct gccgcctctg caacaagtac cgcgtgggcc acgtggacgt gccaccagtg    1560
ccagaccact ccgacaagga ggccttccag aggaagaagc tcggctgcca gctcctcggc    1620
acctacaagc aggtgatctc cgtggtggtc caggccttca tcagcgtggt cgtccaggcg    1680
ttctgaggcg cgccacttaa ataatgtatg aaataaaagg atgcacgcat agtgacatgc    1740
taatcactat aatgtgggca tcaaagttgt gtgttatgtg taattactag ttatctgaat    1800
aaaagagaaa gaggtcatcc atatttcttt tcctaaagaa atgtcacgtg tctttataat    1860
tctttgatga accagatgca ttttattaac caaatccata tacatataaa tattaatcat    1920
atataattaa tatcaattgg gttagcaaaa caaatctagt ctaggtgtgt tttgctaatt    1980 attggggat agtgcagaaa gaaatctacg ttctcaataa ttcagataga aacttaata    2040 aagtgagata atttacatag attgctttta tcctttgata catgtgaaac catgcatgat    2100
ataaggaaaa tagatagata agcttggcat gcctgcaggt ccgattgaga cttttcaaca    2160
aagggtaata tccggaaacc tcctcggatt ccattgccca gctatctgtc actttattgt    2220
gaagatagtg gaaaggaag gtggctccta caaatgccat cattgcgata aggaaaggc     2280 catcgttgaa gatgcctctg ccgacagtgg tcccaaagat ggaccccac ccacgaggag    2340 caccgtggaa aagaagacg ttccaaccac gtcttcaaag caagtggatt gatgtgatgg    2400
ccgattgaga cttttcaaca aagggtaata tccggagacc tcctcggatt ccattgccca    2460
gctatctgtc actttattgt gaagatagtg gaaaggaag gtggctccta caaatgccat    2520
cattgcgata aggaaaggc catcgttgaa gatgcctctg ccgacagtgg tcccagagat    2580 ggaccccac ccacgaggag catcgtggaa aagaagacg ttccaaccac gtcttcaaag     2640
caagtggatt gatgtgatat ctccactgac gtaagggatg acgcacaatc ccactatcct    2700
tcgcaagacc cttcctcaat ataaggaagt tcatttcatt tggagaggag atcttttat     2760 tttaattttt ctttcaaata cttcccgggc tctagagcg atcgcgggat cccgcgatcg    2820
ccaccatgaa gaagcagag cttaccgcca cctccgtgga gaagttcctc atcgagaagt    2880
tcgactccgt gtccgacctc atgcaactct ccgagggcga ggagtccagg gccttctctt    2940
tcgacgtggg cggcagggc tacgtgctca gggtgaactc ctgcgccgac ggcttttaca    3000
aggaccgcta cgtgtaccgc cacttcgcct ctgccgccct cccaatccca gaggtggctc    3060
gacatcggcg agttctctga gtctctcacc tactgcatct ctaggagggc ccagggcgtg    3120
accctccagg acctcccaga gaccgagctt ccagccgtgc tgcaggtaaa tttctagttt    3180
ttctccttca ttttcttggt taggaccctt ttctctttt attttttga gctttgatct     3240 ttctttaaac tgatctattt tttaattgat tggttatggt gtaaatatta catagcttta    3300
actgataatc tgattacttt atttcgtgtg tctatgatga tgatgataac tgcagccggt    3360
cgccgaggcc atggacgcca tcgccgctgc cgatctctcc cagacctccg gcttcggccc    3420
attcggccct cagggcatcg gccagtacac cacctggagg gacttcatct cgccattgc     3480 cgacccacat gtgtaccatt ggcagaccgt gatggacgat accgtgtctg cctctgtggc    3540
ccaggccctc gacgagctta tgctctgggc cgaggactgc ccagaggtga ggcacctcgt    3600
gcacgccgac ttcggctcca acaacgtgct caccgacaac ggcaggatca ccgccgtgat    3660
cgattggtct gaggccatgt tcggcgactc tcagtacgag gtggccaaca tcttcttctg    3720
gcgcccatgg ctcgcttgca tggagcagca gaccagatac ttcgagagga ggcacccaga    3780
gcttgccggc tccccaaggc tcagggctta catgctcagg atcggcctcg atcagctcta    3840
```

-continued

```
ccagtctctc gtggacggca acttcgacga tgccgcctgg gctcagggca ggtgcgatgc    3900
catcgtgagg tctggcgctg gcaccgtggg caggacccag atcgccagga ggtctgccgc    3960
cgtgtggacc gatggctgcg tggaggtgct cgccgactct ggcaacagga ggccatccac    4020
caggccaagg gccaaggagt gagaagcaga tctcgagcgt tcaaacattt ggcaataaag    4080
tttcttaaga ttgaatcctg ttgccggtct tgcgatgatt atcatataat ttctgttgaa    4140
ttacgttaag catgtaataa ttaacatgta atgcatgacg ttatttatga gatgggtttt    4200
tatgattaga gtcccgcaat tatacattta atacgcgata gaaaacaaaa tatagcgcgc    4260
aaactaggat aaattatcgc gcgcggtgtc atctatgtta ctagatcgac gtc           4313
```